US009744323B2

(12) United States Patent
Hoftman et al.

(10) Patent No.: US 9,744,323 B2
(45) Date of Patent: Aug. 29, 2017

(54) SYSTEM AND METHODS FOR LUNG ISOLATION AND ONE LUNG VENTILATION

(71) Applicant: THE REGENTS OF THE UNIVERSITY OF CALIFORNIA, Oakland, CA (US)

(72) Inventors: Nir N. Hoftman, Los Angeles, CA (US); Aman Mahajan, Sherman Oaks, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 447 days.

(21) Appl. No.: 14/560,873

(22) Filed: Dec. 4, 2014

(65) Prior Publication Data
US 2015/0151063 A1 Jun. 4, 2015

Related U.S. Application Data

(63) Continuation of application No. PCT/US2013/046019, filed on Jun. 14, 2013.
(Continued)

(51) Int. Cl.
A61M 11/00 (2006.01)
A61M 16/04 (2006.01)
(Continued)

(52) U.S. Cl.
CPC ....... A61M 16/0404 (2014.02); A61B 1/0051 (2013.01); A61B 1/05 (2013.01);
(Continued)

(58) Field of Classification Search
CPC .......... A61M 16/0404; A61M 16/0434; A61M 16/0057; A61M 16/0816; A61M 16/0463; A61M 16/20; A61M 16/0488; A61M 16/0825; A61M 16/0443; A61M 16/0833; A61M 16/0445; A61B 1/05; A61B 1/2676; A61B 1/0051
See application file for complete search history.

(56) References Cited

U.S. PATENT DOCUMENTS 5,135,490 A * 8/1992 Strickland ......... A61M 16/0463
128/898
5,707,352 A * 1/1998 Sekins .................. A61F 7/123
128/200.24
(Continued)

FOREIGN PATENT DOCUMENTS

WO 9637250 A1 11/1996

OTHER PUBLICATIONS

Korean Intellectual Property Office (KIPO), International Search Report and Written Opinion issued Oct. 15, 2013, counterpart PCT international application No. PCT/US2013/046019, pp. 1-14, with claims searched, pp. 15-20.

Primary Examiner — Steven Douglas
(74) Attorney, Agent, or Firm — O'Banion & Ritchey LLP; John P. O'Banion

(57) ABSTRACT

A lung isolation system configured for selective isolation and ventilation of the lung in conjunction with a standard endotracheal tube. The system includes an expandable bronchial isolation tube comprising a collapsible nitinol frame, a bifurcated adapter, and a steerable optical stylet.

26 Claims, 16 Drawing Sheets

Related U.S. Application Data

(60) Provisional application No. 61/660,149, filed on Jun. 15, 2012.

(51) Int. Cl.

| | | |
|---|---|---|
| *A61B 1/005* | (2006.01) | |
| *A61B 1/05* | (2006.01) | |
| *A61B 1/267* | (2006.01) | |
| *A61M 16/00* | (2006.01) | |
| *A61M 16/20* | (2006.01) | |
| *A61M 16/08* | (2006.01) | |

(52) U.S. Cl.
CPC ....... *A61B 1/2676* (2013.01); *A61M 16/0057* (2013.01); *A61M 16/0434* (2013.01); *A61M 16/0463* (2013.01); *A61M 16/0488* (2013.01); *A61M 16/0816* (2013.01); *A61M 16/20* (2013.01); *A61M 16/0443* (2014.02); *A61M 16/0445* (2014.02); *A61M 16/0825* (2014.02); *A61M 16/0833* (2014.02)

(56) References Cited

U.S. PATENT DOCUMENTS

| | | | |
|---|---|---|---|
| 5,954,636 A | 9/1999 | Schwartz | |
| 2004/0144387 A1* | 7/2004 | Amar | A61M 16/04 128/207.14 |
| 2004/0158228 A1 | 8/2004 | Perkins | |
| 2005/0205097 A1* | 9/2005 | Kyle | A61M 16/04 128/207.14 |
| 2009/0260625 A1 | 10/2009 | Wondka | |
| 2011/0186053 A1 | 8/2011 | Pol | |
| 2013/0204082 A1* | 8/2013 | Fischer, Jr. | A61M 16/0833 600/104 |
| 2014/0311497 A1* | 10/2014 | Daly | A61M 16/04 128/207.15 |
| 2017/0072154 A1* | 3/2017 | Hoftman | A61M 16/0816 |

\* cited by examiner

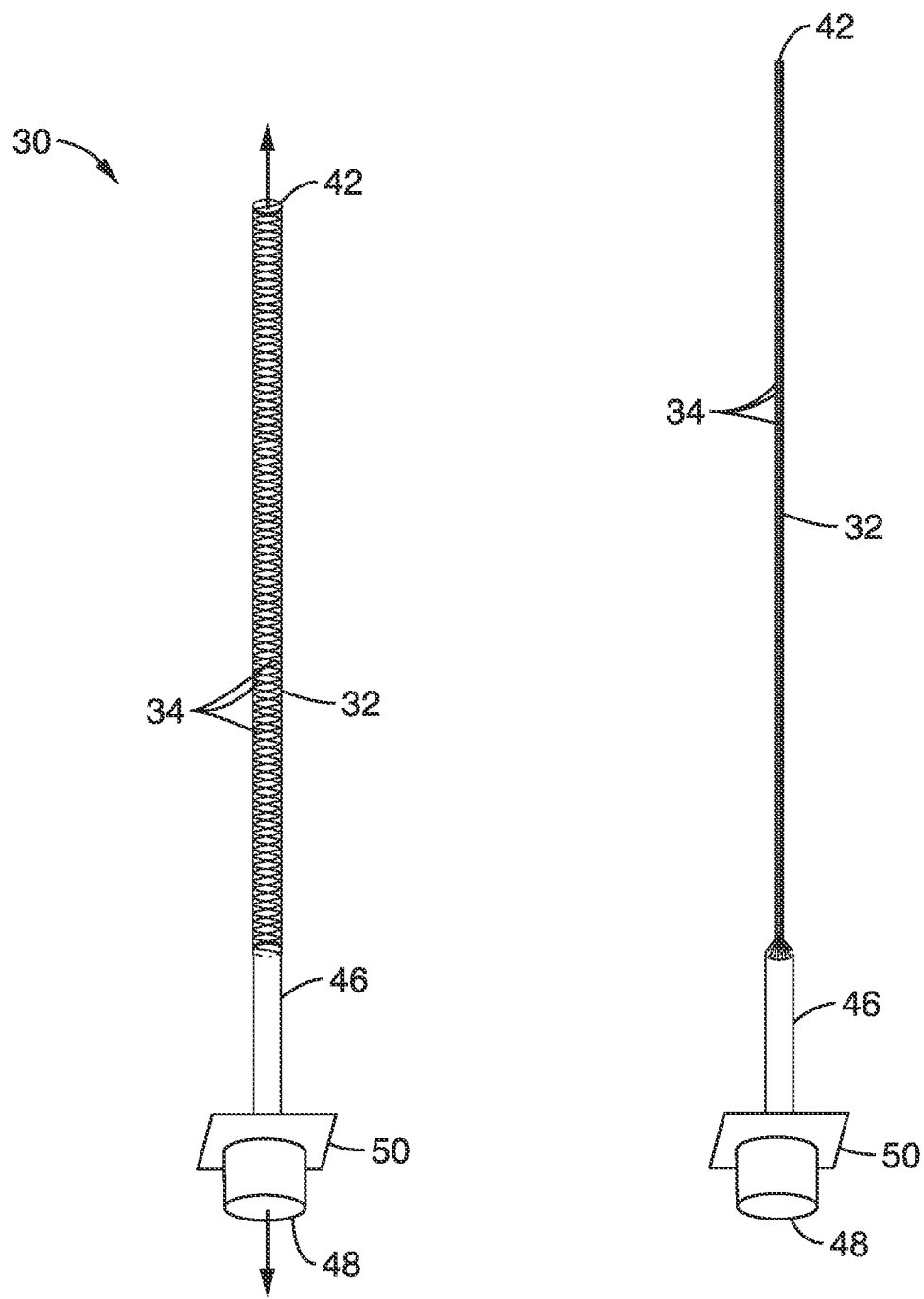

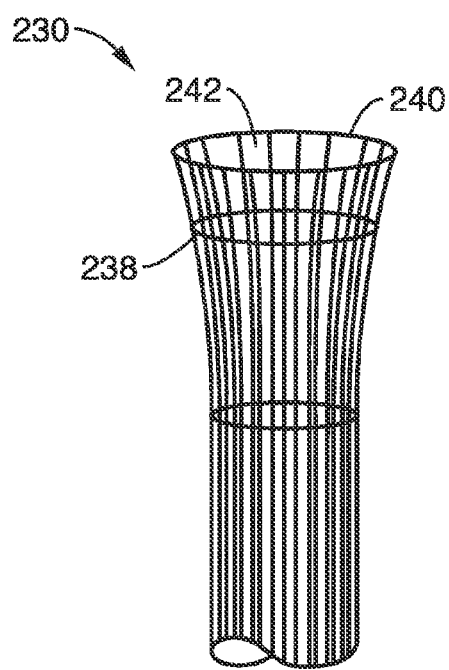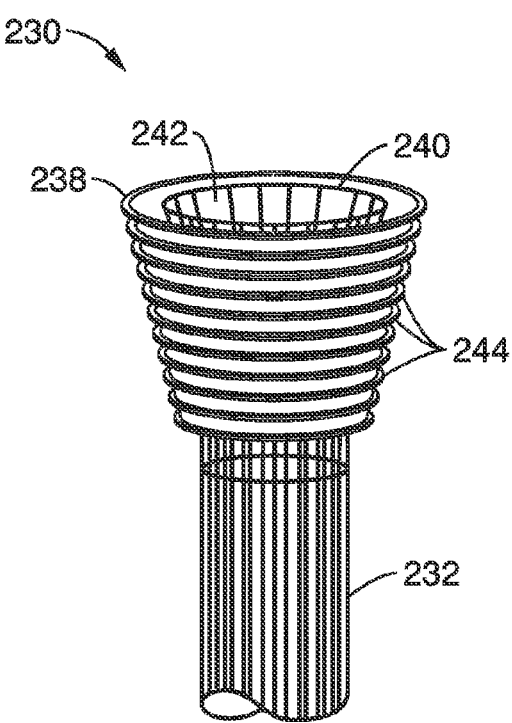
FIG. 14A
FIG. 14B

SYSTEM AND METHODS FOR LUNG ISOLATION AND ONE LUNG VENTILATION

CROSS-REFERENCE TO RELATED APPLICATIONS

This application is a 35 U.S.C. §111(a) continuation of PCT international application number PCT/US2013/046019 filed on Jun. 14, 2013, incorporated herein by reference in its entirety, which claims priority to, and the benefit of, U.S. provisional patent application Ser. No. 61/660,149, filed on Jun. 15, 2012, incorporated herein by reference in its entirety. Priority is claimed to each of the foregoing applications.

The above-referenced PCT international application was published as PCT International Publication No. WO 2013/188845 on Dec. 19, 2013, which publication is incorporated herein by reference in its entirety.

STATEMENT REGARDING FEDERALLY SPONSORED RESEARCH OR DEVELOPMENT

Not Applicable

INCORPORATION-BY-REFERENCE OF MATERIAL SUBMITTED IN A COMPUTER PROGRAM APPENDIX

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without

BACKGROUND

1. Technical Field

The present disclosure relates generally to ventilation, and more particularly to lung isolation and single lung ventilation.

2. Background Discussion

Lung isolation and single lung ventilation are routinely instituted during thoracic surgery. Surgery involving the lung or the contents of the thorax often requires cessation of ventilation to one lung for two main reasons: 1) to keep the lung immobile while surgery on it is performed, 2) to deflate the lung for better visualization of thoracic structures. Other indications for lung isolation include: 1) containment of unilateral pulmonary bleeding or infection, 2) management of bronchopleural fistula or other pulmonary air leaks. Today, the gold standard for lung isolation is the double lumen endotracheal tube (DLT). Modern disposable polyvinylchloride (PVC) DLTs are modifications of the original Robert-Shaw tube introduced more than sixty years ago. These endotracheal tubes contain two separate lumens, one for each lung, and ventilation is separated with the use of endotracheal and endobronchial balloon cuffs. Drawbacks to the use of DLTs include: 1) difficult insertion due to the device's size and design, 2) need to exchange the tube to a single lumen tube at the end of the case when post-operative intubation is required, and 3) limited compatibility with bronchoscopes and suction catheters due to the DLT's small lumen diameters.

Given these drawbacks, there exists an alternative approach to lung isolation involving balloon tipped endobronchial catheters collectively known as "bronchial blockers." These devices are deployed through standard large bore endotracheal tubes, utilizing a connector included within the kit. Upon positioning of the balloon tipped catheter into the proper bronchus, balloon inflation leads to unilateral cessation of ventilation. Several variations of this device are currently available for clinical use. Major drawbacks of this device include: 1) inability to quickly and easily alternate ventilation from one lung to the other, 2) easy balloon dislodgement, which not only disrupts lung isolation, but has also led to serious morbidity, 3) inability to suction the isolated lung.

Confirmation of correct placement and positioning of either double lumen tubes or bronchial blockers requires visualization of the tracheobronchial tree anatomy. This is typically achieved utilizing a fiber optic or distal chip pulmonary bronchoscope. Given the possibility of intraoperative dislodgement/malposition, the bronchoscope must remain available for the entire case, tying up considerable resources.

BRIEF SUMMARY

The technology of the present disclosure, which we also refer to herein as the lung isolation system, achieves reliable lung isolation while utilizing a standard large-bore, single-lumen endotracheal tube. In one embodiment, the system comprises three main components: 1) an expandable bronchial isolation tube (EBIT); 2) an adapter; and 3) a steerable optical stylet. The system enables true dual lumen lung isolation/ventilation utilizing a co-axial design, thus enabling all the benefits of both a double lumen tube and a bronchial blocker, without either's downsides. It also incorporates a video visualization system, thus precluding the need for traditional fiber optic bronchoscopy.

Further aspects of the technology of the present disclosure will be brought out in the following portions of the specification, wherein the detailed description is for the purpose of fully disclosing preferred embodiments of the technology of the present disclosure without placing limitations thereon.

BRIEF DESCRIPTION OF THE SEVERAL VIEWS OF THE DRAWING(S)

The technology of the present disclosure will be more fully understood by reference to the following drawings which are for illustrative purposes only:

FIG. 2A and FIG. 2B show the EBIT of FIG. 1 in an expanded configuration and an axially loaded, collapsed "catheter" configuration, respectively.

FIG. 14A and FIG. 14B show the EBIT of FIG. 13 in an expanded configuration and an axially loaded, collapsed "catheter" configuration, respectively.

DETAILED DESCRIPTION

The description below with respect to FIG. 1 through FIG. 10 details a preferred embodiment of a lung isolation system configured to operate in conjunction with a standard plastic disposable endotracheal tube in accordance with the technology of the present disclosure. FIG. 11 through FIG. 17 illustrate an alternative embodiment of a lung isolation system configured to operate with a modified endotracheal tube in accordance with the technology of the present disclosure. It is appreciated that components of each of these embodiments may be used interchangeably, where appropriate.

Figure 1:
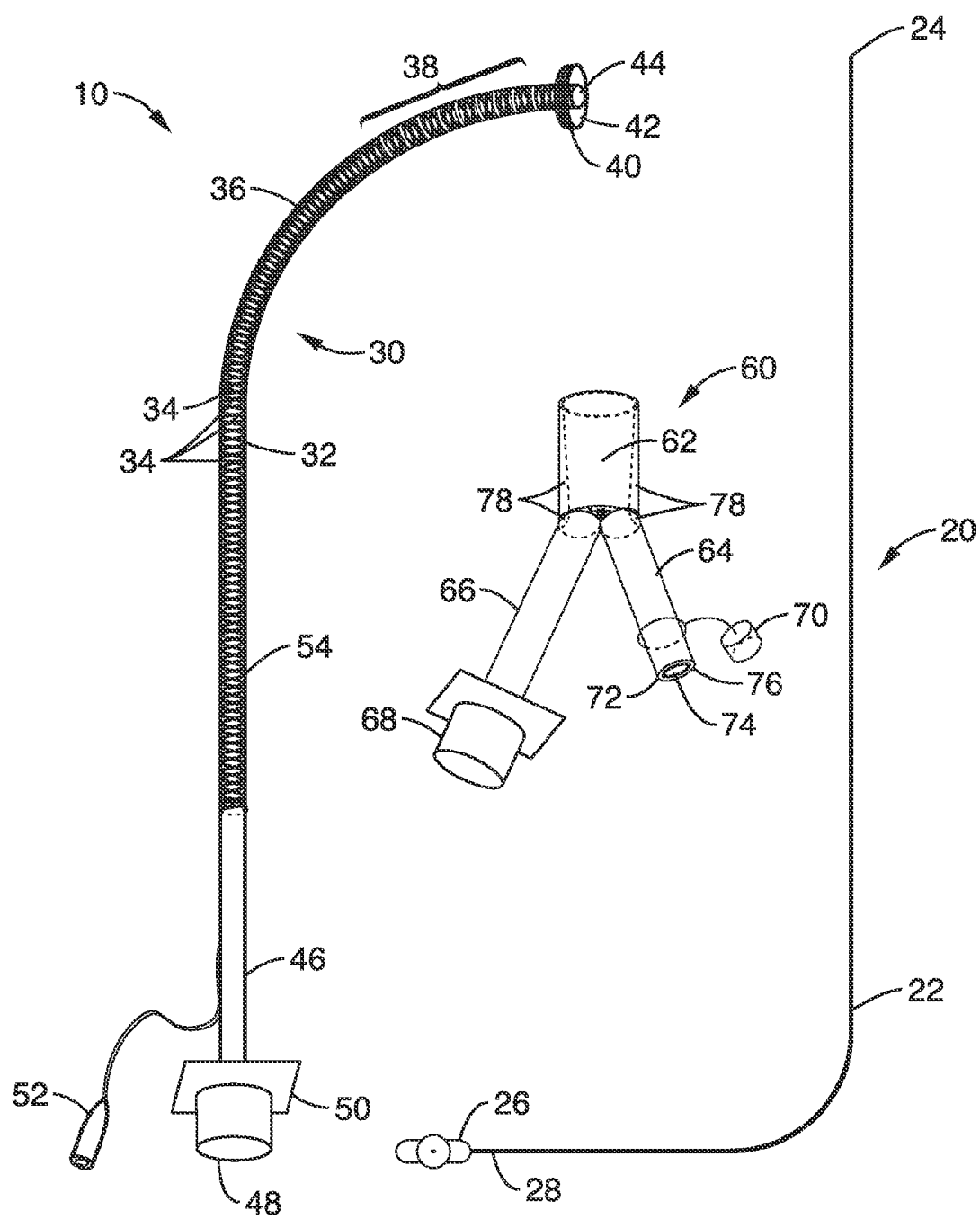
FIG. 1 is a schematic view of a lung isolation system comprising an expandable bronchial isolation tube (EBIT), an adapter, and steerable optical stylet.

Referring to FIG. 1, lung isolation system 10 comprises three main components: 1) an expandable bronchial isolation tube (EBIT) 30; 2) a bifurcated adapter 60; and 3) a steerable optical stylet 20.

The EBIT 30 is an elongate (e.g. 50 cm long) endotracheal tube (having approximately a 5 mm internal diameter) that is primarily composed of two main components: a proximal member 46 comprising a rigid plastic tube (e.g. 10 cm long (5 mm ID) terminating proximally at a universal (e.g. 15 mm) connector 50.

Attached to the proximal member 46 is a flexible distal member 32 that is approximately 40 cm long (5 mm ID) and is attached to the distal extent of the proximal member via an adhesive or like fastening means. The proximal member 46 and flexible distal member 32 form one contiguous channel 36 emanating from proximal opening 48 in connector 50 to distal opening 44 at the distal end 42 of the distal member 32.

In a preferred embodiment, flexible distal member 32 comprises a nitinol tube formed of individual wire frame segments 34 onto which a silicone (or other membranous material) skin 54 is embedded. This membranous material 54 seals the spaces between the individual wires 34 that make up the nitinol-braided tube so that the tube is thus able to transport and conduct gases without leaking. A portion of the distal end (e.g. last 10 cm) of the tube has a circumferential ruler 38 printed on the outside diameter to aid in depth measurement.

Referring now to FIG. 2A and FIG. 2B, the nitinol wire frame 34 of EBIT 30 preferably comprises a memory such that it springs to the expanded, tubular configuration in the resting state as shown in FIG. 2A. However, when in an axially loaded configuration as shown in FIG. 2B, the frame 34 collapses and lengthens, such that it forms a catheter with an obliterated lumen and a much-reduced external diameter for easy insertion and positioning. Generally, a continuous input of force is required to keep the EBIT 30 in the closed configuration (offsetting the natural tendency of the frame 34 to spring into the expanded tubular shape). The EBIT nitinol component 34 can also be distorted (e.g. bent, as shown in FIG. 1) or compressed, and regains its original configuration once this force is withdrawn.

Figure 3A:
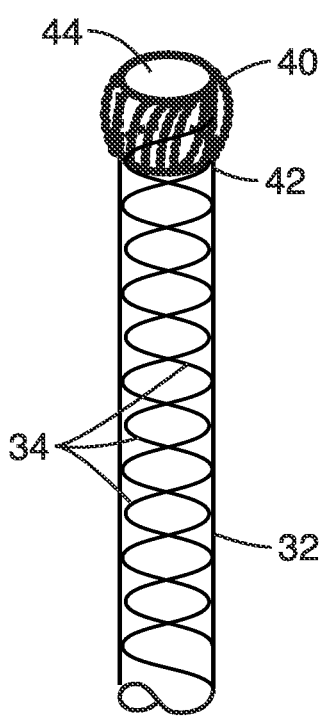
FIG. 3A and FIG. 3B show the EBIT of FIG. 1 in collapsed "catheter" configuration and expanded configuration, respectively.
Figure 3B:
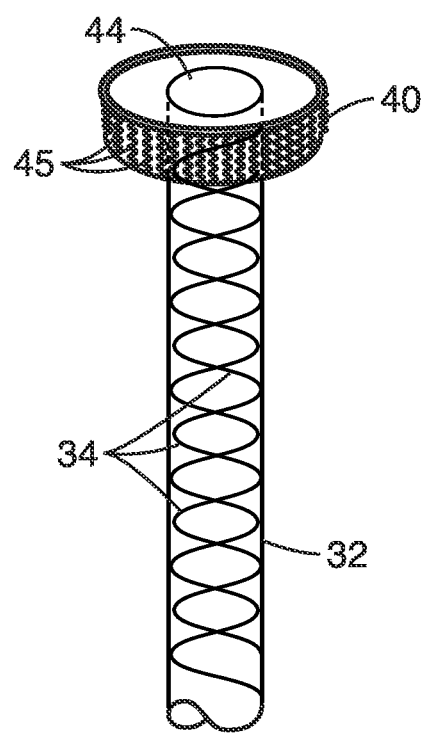

Referring now to FIG. 3A and FIG. 3B, radially surrounding the EBIT distal tip 42 is an expandable member (e.g. inflatable balloon cuff) 40 configured to create an ideal seal with internal tubular anatomy such as the mainstem bronchus. Using balloon cuff valve 52, air may be delivered to balloon 40 once the distal 42 end of the EBIT is delivered to the target location within the body. The balloon cuff 40 then expands from the collapsed configuration shown in FIG. 3A, to the expanded configuration shown in FIG. 3B Inflatable balloon cuff 40 is cylindrical in shape and comprises a material, coating, or roughened exterior surface 45 that is coarse rather than smooth. The cylindrical shape of the EBIT inflatable balloon cuff 40 maximizes the flat surface in contact with the airway when inflated. The balloon's length (approximately 1 cm) allows it to fit into short bronchi without herniating, while its shape still ensures ample contact area. Furthermore, the balloon's surface texture 45 is coarse due to its material and design (ridges or bumps may be added); this texture creates increased friction at its interface with the airway, reducing the likelihood of accidental dislodgement. This configuration reduces possible airway injury from cuff over-inflation by requiring a lower perpendicular force (and thus cuff inflation pressure) to seal gaps and resist dislodgement and migration.

The EBIT 30 is generally a single use component that is to be discarded at the end of a case.

In an alternative design (not shown), the EBIT 30 distal segment 32 comprises a steel spiral-reinforced plastic tube. This design would differ from the previously described EBIT 30 in that it would be rigid in shape, non-stretchable, non-deformable or collapsible. This device would be inserted in the previously described manner, but would not be axially loaded and stretched like the nitinol EBIT, because it cannot deform in such a manner. The dimensions of the steel reinforced EBIT would be similar to the expanded nitinol EBIT.

Referring back to FIG. 1, the adapter 60 allows for the integration of the system 10 with a standard large bore single lumen endotracheal tube 140 and mechanical ventilator 130

Figure 8:
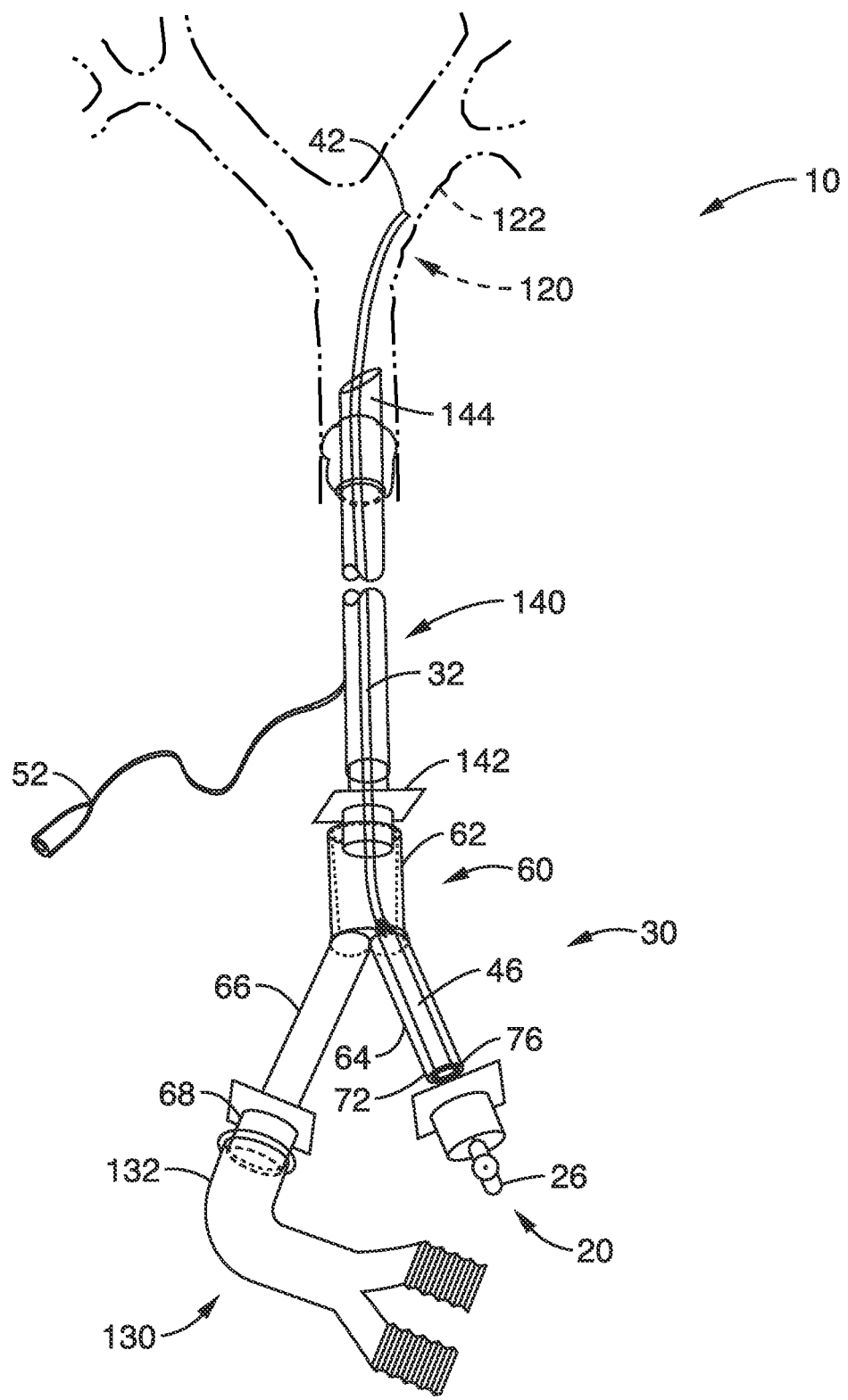
FIG. 8 is a schematic view of a lung isolation system of FIG. 1 being steered into the right mainstem bronchus of a patient for positioning.

(see also FIG. 8). In a preferred embodiment, the adapter 60 comprises a distal tube 62 that bifurcates, to a modified "Y" configuration.

The left hand lumen 66 contains a universal endotracheal tube connector 68 (e.g. 15 mm) that is configured to attach to the mechanical ventilator 130 during use.

The right hand lumen 64 comprises the conduit aperture 74 through which the EBIT 30 is inserted and deployed. Within this lumen is contained a circumferential O-ring or seal 76 disposed at the opening at proximal end 72. The O-ring 76 is configured to surround and form a seal with proximal section 46 of the inserted EBIT 30 when installed, sealing any gaps, and thus preventing gas leakage during positive pressure ventilation. When the EBIT 30 is removed, a rubber cap 70 may be fit over the orifice 74 to prevent gas leakage. Internal slopes 78 on the inside surfaces of the adapter 60 help guide inserted catheters into the center of the lumen, thus reducing catheter "hold up." In a preferred embodiment, the adapter 60 is a single use component that is to be discarded at the end of a case.

Figure 4:
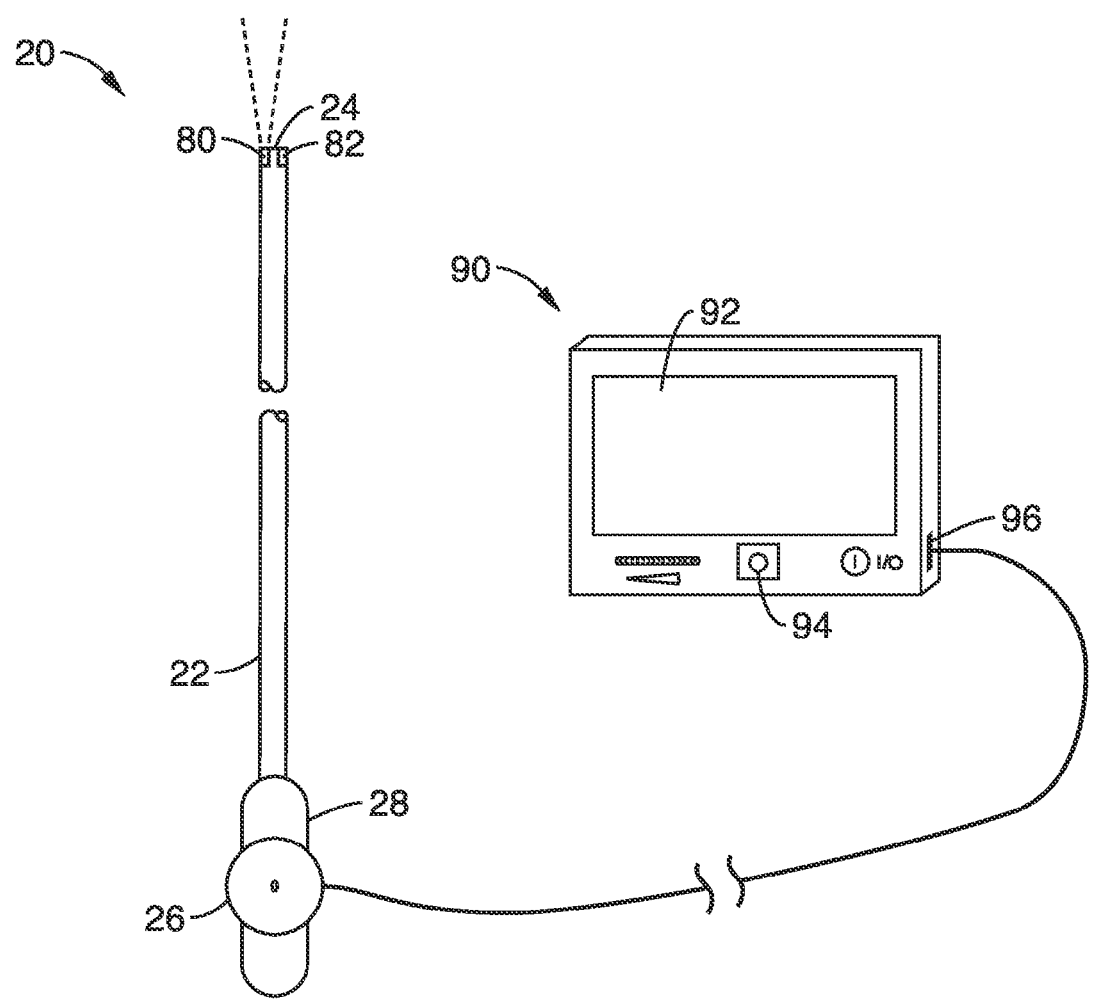
FIG. 4 is a schematic diagram of the steerable optical stylet steering mechanism and corresponding display.

FIG. 4 illustrates a steerable optical stylet 20 comprising a semi-rigid, malleable stylet 22 with a steerable distal tip 24. The tip 24 preferably houses a video chip camera 82 as well as an LED based battery powered light source 80 for illuminating and imaging the target anatomy. The steerable optical stylet 20 interfaces either via wired (e.g. USB port 96) or wireless (not shown) connection with a video system 90 comprising a display 92 and recorder/memory 94 for viewing and storing video images of the target anatomy.

The steerable optical stylet 20 generally serves two main purposes: 1) to steer and position the EBIT 30 into the proper location in the tracheobronchial tree, and 2) to monitor the position of the EBIT throughout the procedure.

Figure 5:
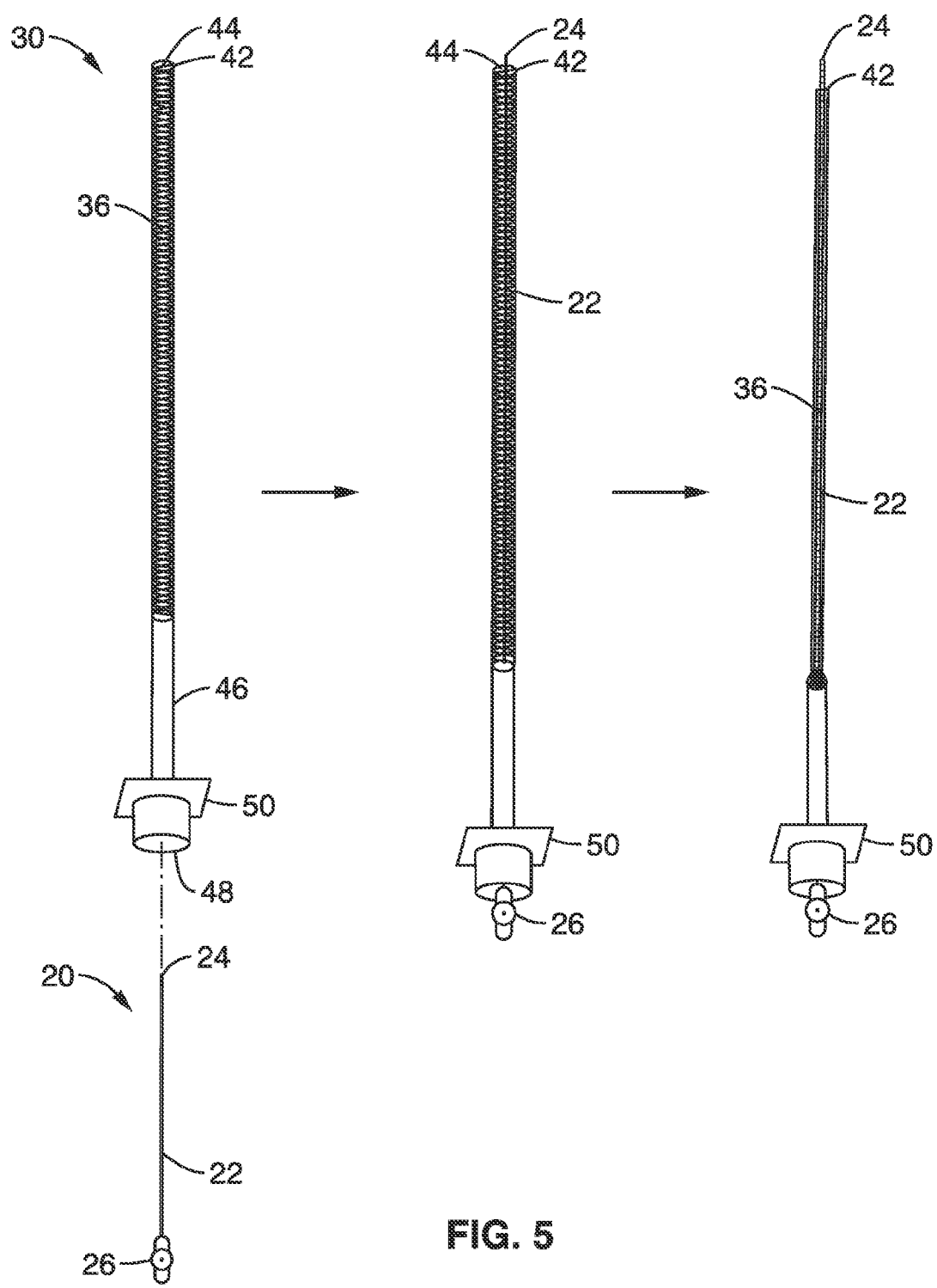
FIG. 5 is a schematic diagram showing insertion of the steerable optical stylet into the EBIT and subsequent collapse of the EBIT around the steerable optical stylet.

Referring now to FIG. 5, to position the EBIT 30, the steerable optical stylet 20 is inserted into its lumen 36 via aperture 48 of connector 50 so that the distal tip 24 of the steerable optical stylet 20 extends partway past distal end 42 of the EBIT 30. The EBIT 30 is then axially loaded (see also FIG. 2A and FIG. 2B) such that the distal segment 32 is collapsed over the steerable optical stylet 20 to reduce the insertion profile.

Figures 6A, 6B, 7:
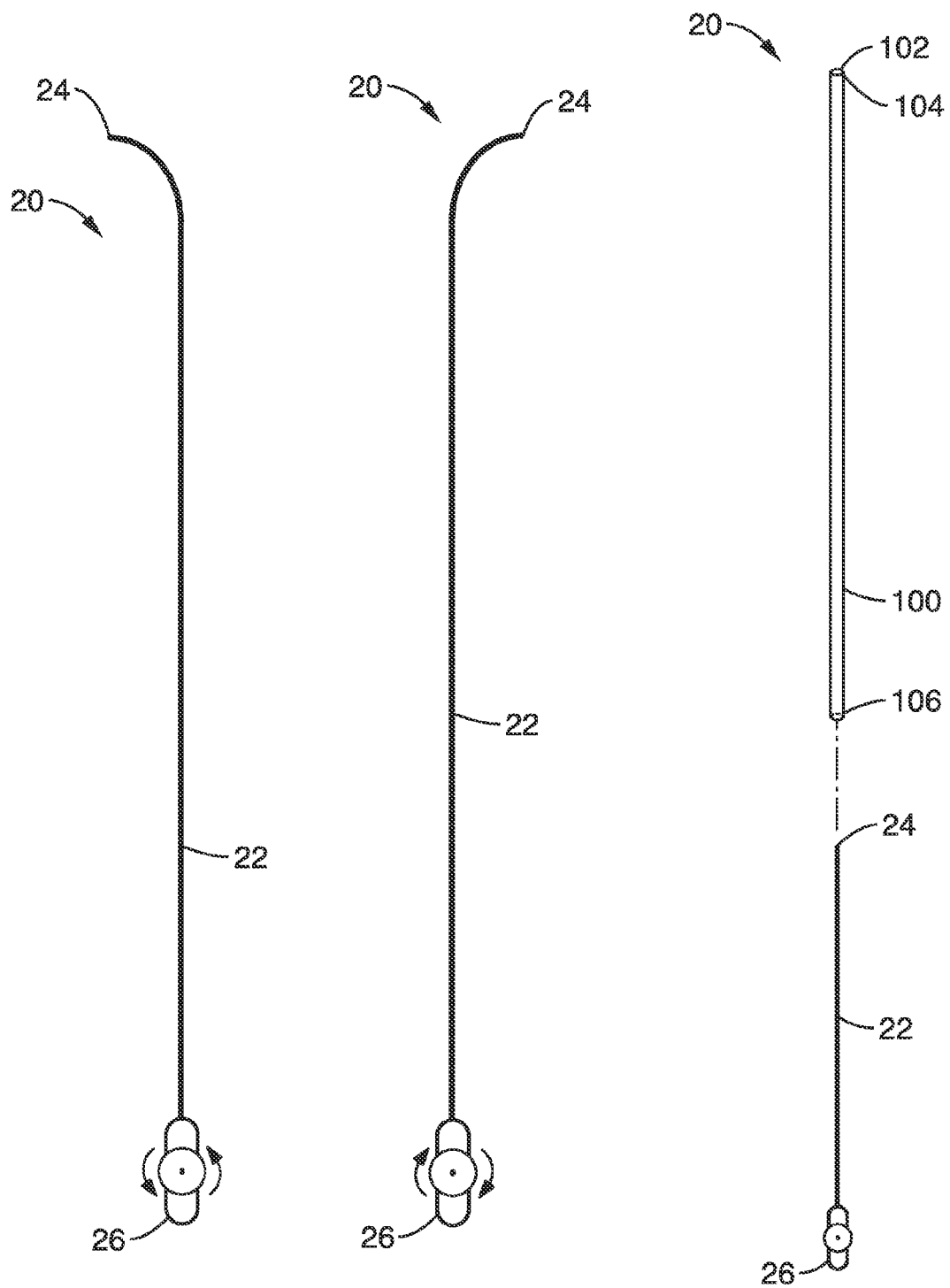
FIG. 6A and 6B are schematic diagrams illustrating manipulation of the steerable optical stylet.
FIG. 7 is a schematic diagram of a disposable protective sleeve installed over the steerable optical stylet.

Referring to FIG. 6A and FIG. 6B, the steerable optical stylet 20 is then used to insert the EBIT 30 much like a fiber optic bronchoscope would be used to insert an endotracheal tube. A lever/wheel 26 at the proximal end 28 (see also FIG. 1) the EBIT 30 head is used to steer the tip 24 in either direction (e.g. left or right) during positioning into the desired bronchus of airway 120 (see FIG. 8).

To monitor EBIT 30 position during the case, the steerable optical stylet 20/EBIT 30 assembly (see FIG. 2B) is inserted into a lumen of the adapter 60 (e.g. left lumen) and positioned above the carina. Video images from the steerable optical stylet 20 may viewed on the small, portable video display 92 that also allows for storage of recorded videos and photos via recorder 94. The display 92 may also be connected to a computer (not shown) for permanent data transfer and storage.

Alternatively, video feed from the steerable optical stylet 20 can also be fed to a standard video display. The steerable optical stylet 20 is reusable and thus should be sterilized for reuse.

Alternatively, a disposable sleeve 100 is available that covers the steerable optical stylet 20 during use is shown in FIG. 7. A plastic lens 102 may be disposed at the distal tip 104 of this sleeve 100 to allow for proper video image transmission. Sleeve 100 preferably covers the entire length of the steerable optical stylet 20, such that the proximal end 106 of the sleeve 100 extends all the way to the handle 26. Once used, the sleeve 100 is preferably removed and disposed, and the steerable optical stylet 20 is then ready for use again.

Referring to FIG. 8 through FIG. 12, the lung isolation system 10 enables lung isolation and one-lung ventilation when used in conjunction with a standard large bore single lumen endotracheal tube. When the lung isolation system 10 is deployed through a standard endotracheal tube 140, two effective lumens are created. The assembled device functions as a tube with two lumens, but instead of being parallel, the lumens are arranged in coaxial configuration (i.e. tube within a tube). The internal lumen is comprised of the EBIT 30 central lumen 36, which generally assumes the endobronchial position. The second lumen is comprised of the space created outside of and surrounding the EBIT 36, but within the central lumen of the large bore endotracheal tube 140. As shown in FIG. 8, this circumferential lumen is accessed through the left bifurcation 66 of the adapter 60, and serves as the tracheal lumen.

According to a preferred method of the technology of the present disclosure, patients set to undergo the procedure will first undergo general endotracheal anesthesia, preferably with an 8.0 mm (or larger) endotracheal tube 140. Once the patient is anesthetized and intubated, in one embodiment, the following steps are then taken in sequence:

1) The distal section 62 of the adapter 60 is attached to the connector 142 of the endotracheal tube 140 and ventilator 130 to the connector 68 at the left bifurcation 66 of the adapter 60; the patient is then ventilated in a standard fashion.

2) The EBIT 30 and steerable optical stylet 20 are then configured (e.g. as shown in FIG. 5) for positioning into the airway 120 tracheobronchial tree 122. It can either be positioned into the right mainstem bronchus 126 or left mainstem bronchus 124, as either configuration will allow for one lung ventilation. The clinical decision on which side to place the EBIT 30 is similar to the decision of whether to use a left or right sided double lumen endotracheal tube (DLT).

3) The EBIT 30/steerable optical stylet 20 combination is then inserted into the orifice 72 located at the right-sided bifurcation 64 of the adapter 30. This orifice serves as the introducer, allowing for seamless insertion of the EBIT 30 into the airway 120 without interruption of ventilation. A rubberized o-ring or diaphragm 76 forms a seal between the EBIT's rigid member 46 and the adapter bifurcation orifice 72 to prevent gas leak. The EBIT 30/steerable optical stylet 20 combination is then inserted under direct video visualization into the airway 120. It is then steered into the desired bronchus; e.g. left for "left sided DLT configuration" or right for "right sided DLT configuration" (as shown in FIG. 8).

Figure 9:
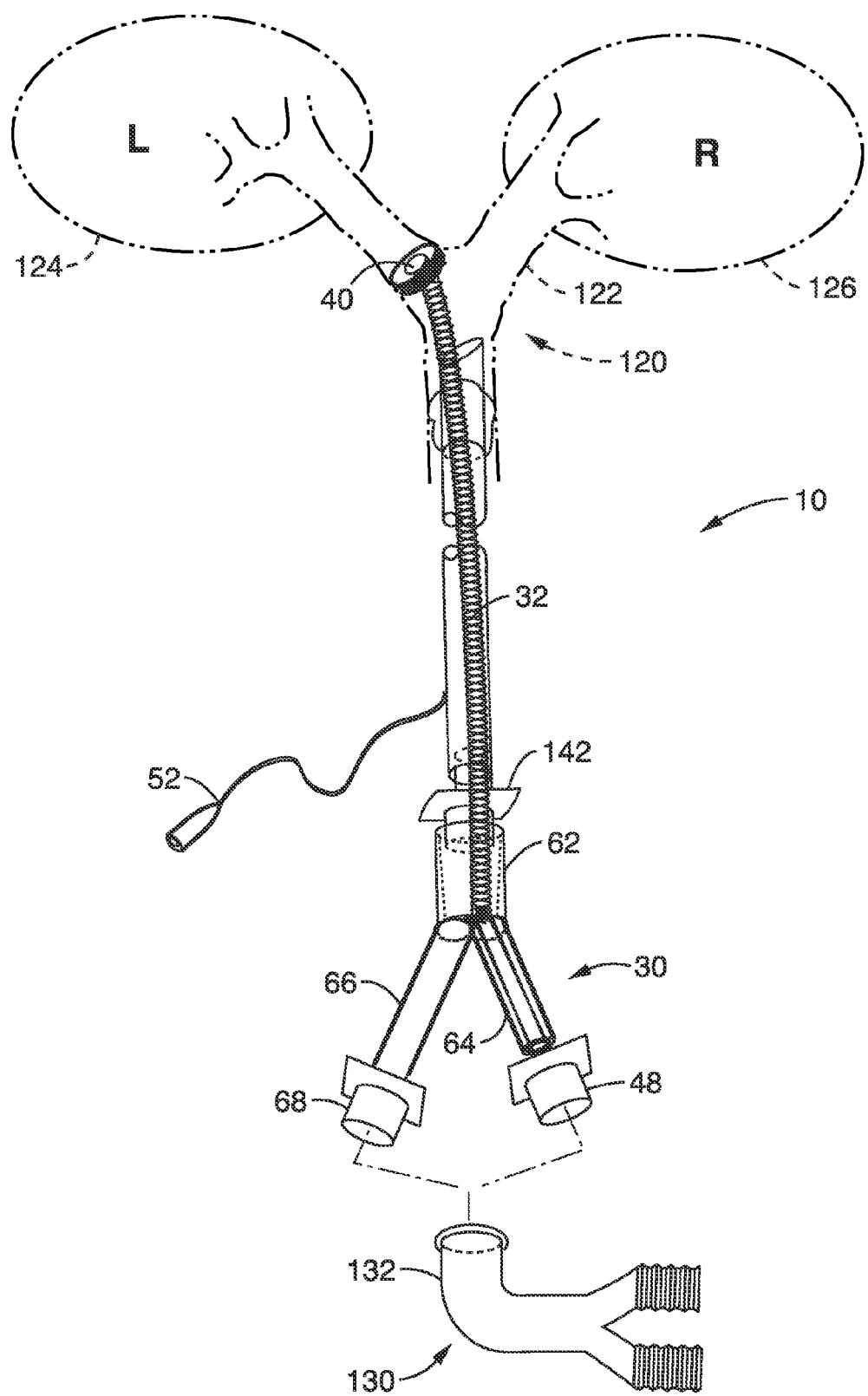
FIG. 9 is a schematic view of a lung isolation system of FIG. 1 being expanded in left mainstem bronchus in a left sided DLT configuration.

4) Once in position, the EBIT 30 is expanded into the tubular configuration (see FIG. 2A, FIG. 9). This may be achieved via a number of means. For example, a circumferential sheath (not shown) may be used to hold the nitinol frame 32 in a compressed state, and removed to allow it to open to the tubular configurations. Alternatively, a wired stylet (similar to stylet 20) may be used to close (lengthen) the frame 32, and then be removed to open it. The balloon cuff 40 is then inflated (e.g. via cuff valve 52) to engage the bronchus wall 122; FIG. 8 demonstrates the "right sided DLT configuration." Lung isolation has now been achieved. The steerable optical stylet 20 is then withdrawn from the expanded EBIT 30.

5) Finally one-lung ventilation is ready to be initiated. The practitioner decides which lung is to be ventilated. It will either be the lung intubated by the EBIT 30, or the other lung (not intubated by the EBIT). If the 15 mm universal connector 48 at the proximal end of EBIT 30 is connected to the ventilator 130, only the lung intubated by the EBIT will be ventilated. If the universal 15 mm connector 68 on the left bifurcation 66 of the adapter 60 is connected to the ventilator coupling 132 instead, only the opposite lung (not intubated by the EBIT) is ventilated (as shown in FIG. 8).

In the example shown in FIG. 9, the EBIT 30 is positioned in the left mainstem bronchus 124 (i.e. "left sided DLT configuration"). Attaching the ventilator 130 to the EBIT 30 at connector 48 would ventilate only the left lung 124, whereas attaching the ventilator 130 to the adapter 60 connector 68 would ventilate only the right lung 126.

Figure 10:
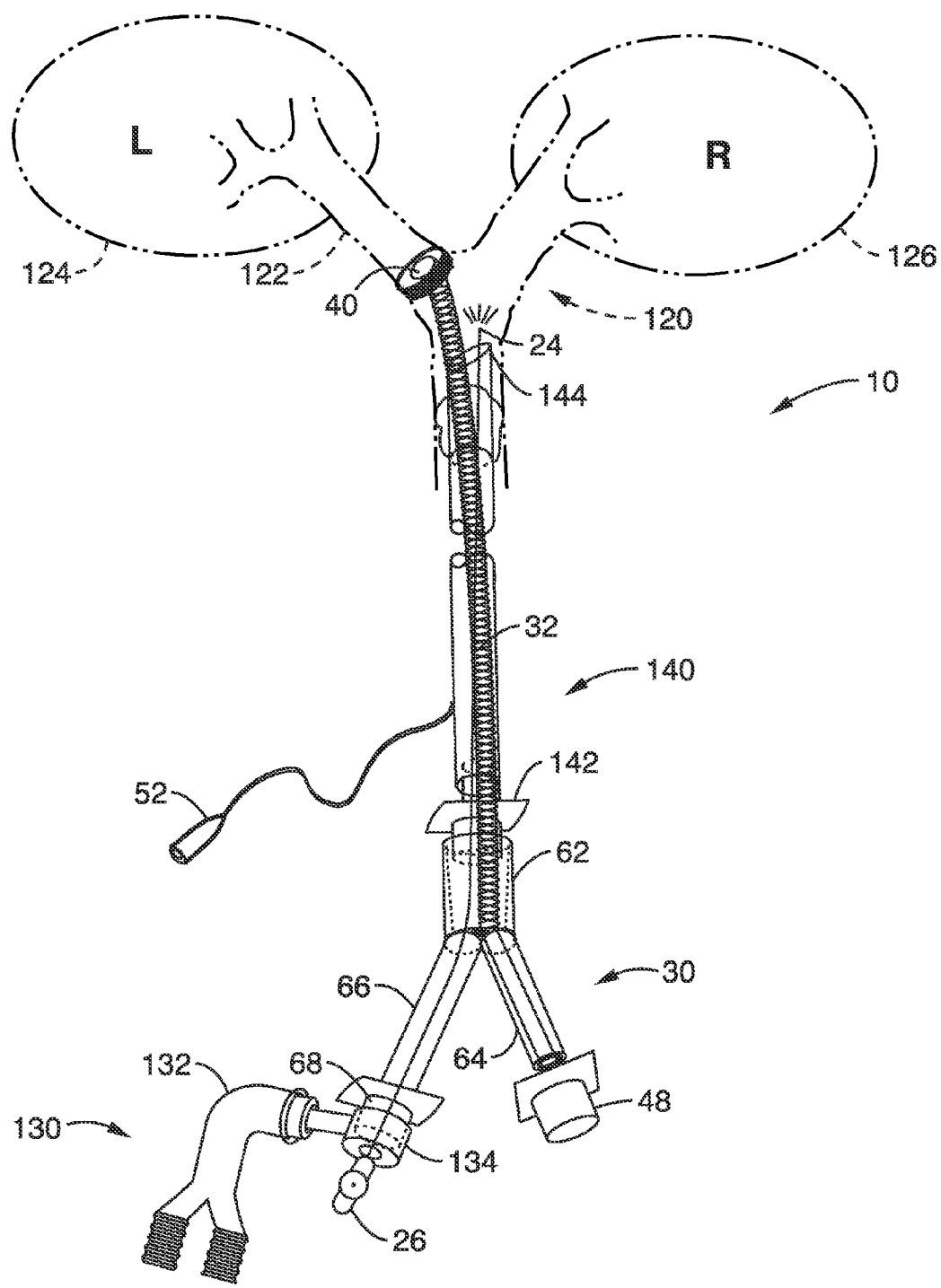
FIG. 10 is a schematic view of the steerable optical stylet of the technology of the present disclosure inserted into adapter left limb for monitoring of EBIT position.

6) Referring to FIG. 10, the EBIT 30 position may also be monitored throughout the case to ensure proper lung isolation by utilizing the steerable optical stylet 20 intraoperatively. The steerable optical stylet 20 distal tip 24 is then positioned beyond distal end 144 of tube 140 above the tracheal bifurcation, such that the EBIT distal end 24 is in clear view for real time monitoring. If the left sided adapter bifurcation 66 is being used for ventilation, the steerable optical stylet 20 is inserted into the left sided bifurcation 66 of the adapter 60 via a standard bronchoscopy swivel adaptor 134 that couples connector 68 to the ventilator coupling 132 to allow for insertion of the steerable optical stylet 20 without interrupting ventilation. The nitinol section 32 of the EBIT 30 allows it to distort around the steerable optical stylet 20 so that its lumen is still patent rather than kinked. Once the steerable optical stylet 20 is removed, the EBIT 30 lumen immediately springs into its original round cross-section.

Figure 11:
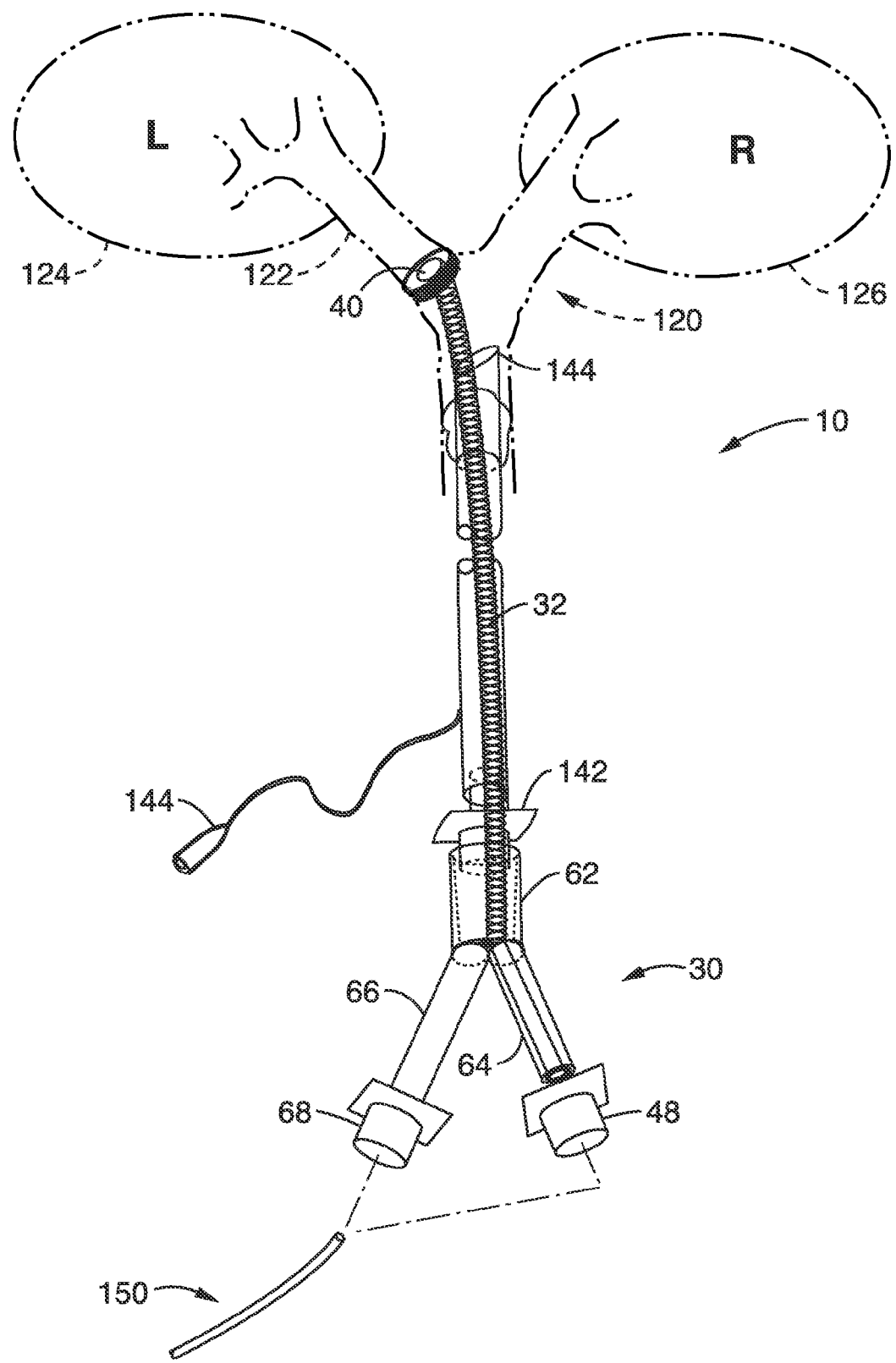
FIG. 11 is a schematic view illustrating use of a suction catheter to be used to suction either lung during the procedure.

7) Referring now to FIG. 11, an airway suction catheter 150 may be inserted into either the EBIT 30 or the adapter left sided bifurcation 66 during one lung ventilation, depending on which lung requires suctioning. Large bore suction catheters can temporarily displace and distort the EBIT's nitinol frame 32, which will spring back into shape once suctioning of the second lumen is complete.

Figure 12:
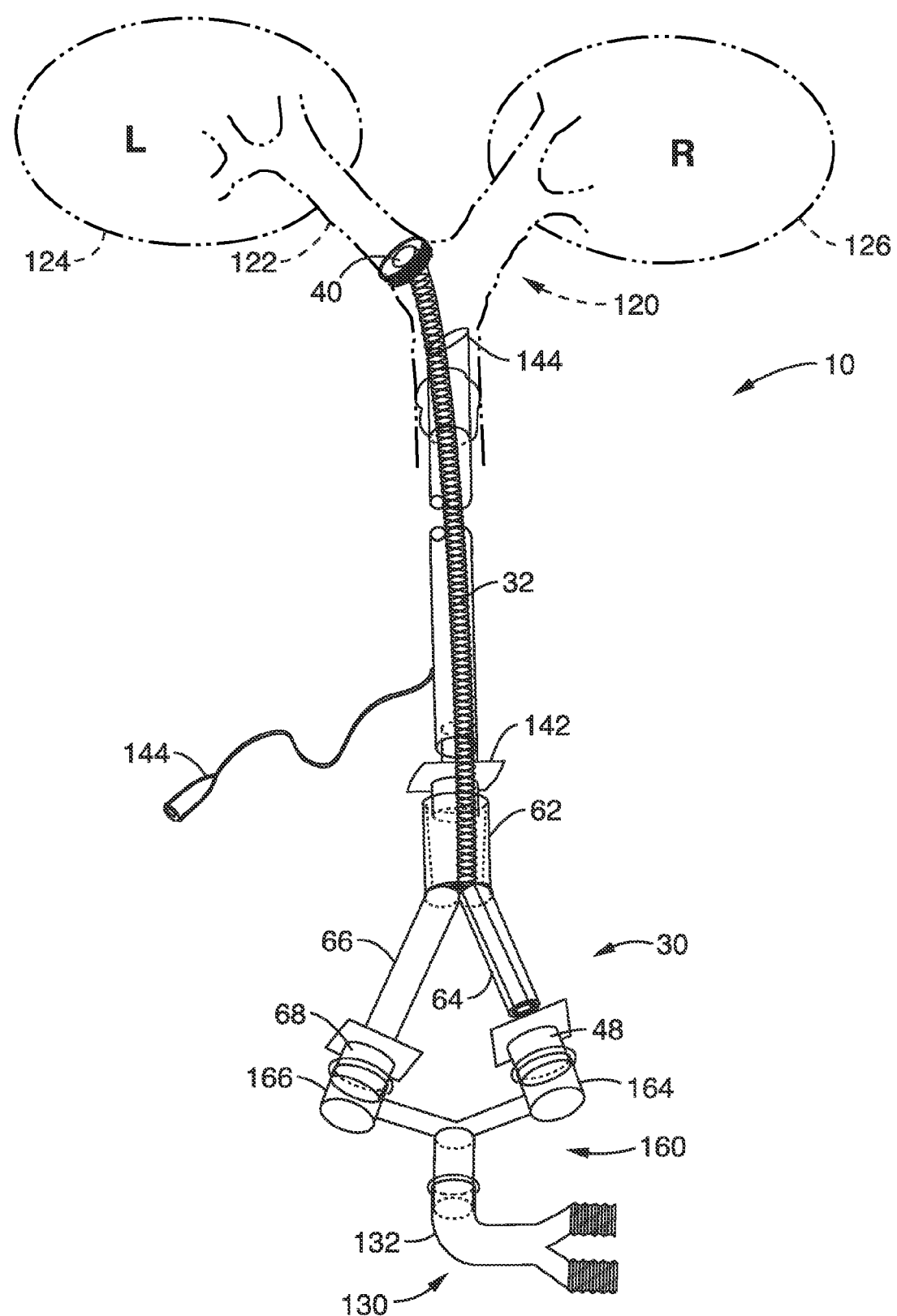
FIG. 12 is a schematic diagram of a configuration showing two-lung ventilation with the EBIT of the technology of the present disclosure in place.

FIG. 12 shows a configuration allowing temporary ventilation of both lungs with attachment of Y piece 160 proximal end 162 to ventilator coupling 132, and ends 166 and 164 to both 15 mm connectors 68 and 48, respectively.

Once lung isolation is no longer necessary, the EBIT balloon 40 is deflated, and the entire EBIT 30 and adapter assembly 60 are removed.

FIG. 13 through FIG. 17 illustrate an alternative embodiment of a lung isolation system 200 configured to operate with a modified endotracheal tube in accordance with the technology of the present disclosure.

Figure 13:
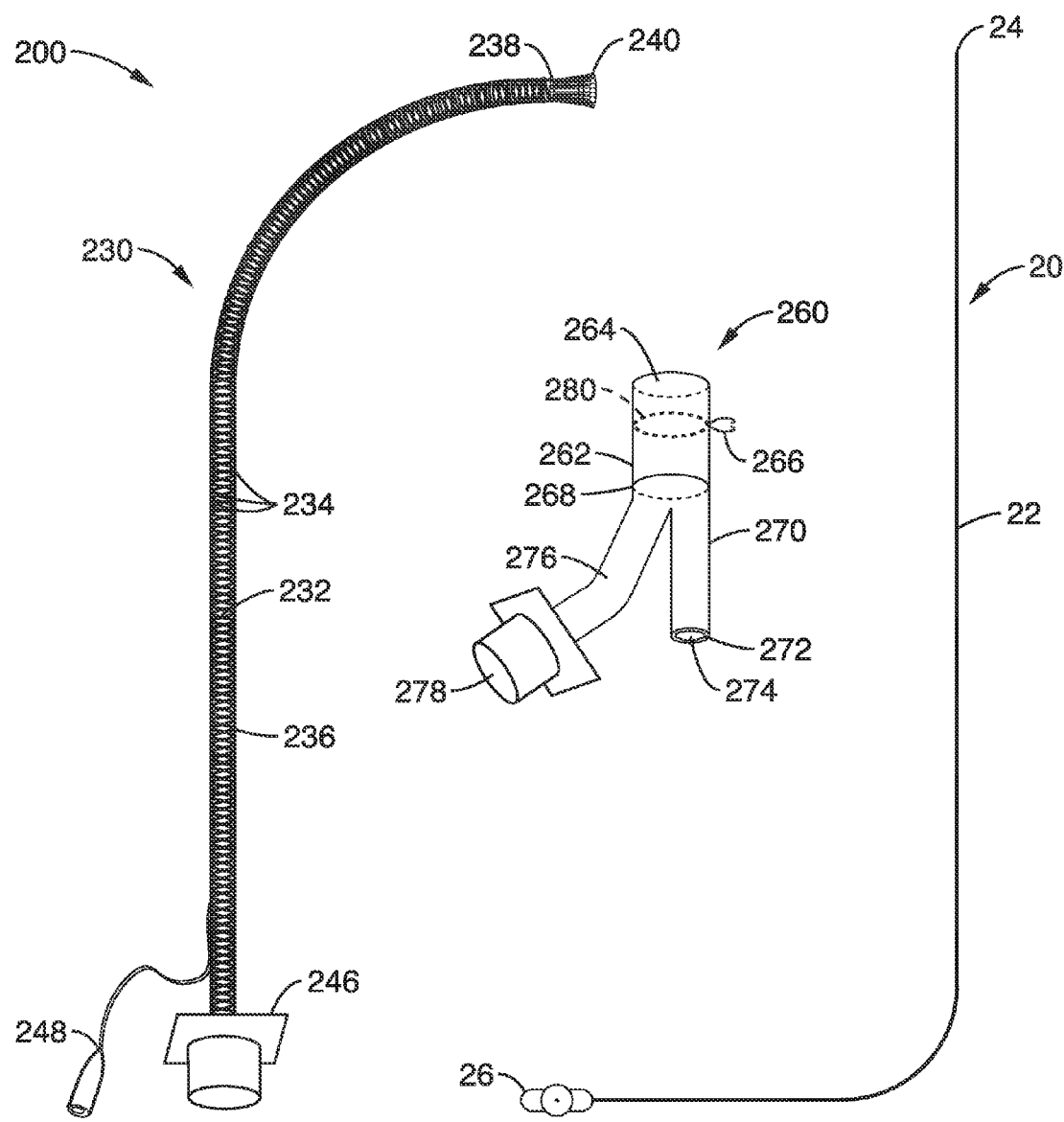
FIG. 13 is a schematic view of an alternative lung isolation system comprising an expandable bronchial isolation tube (EBIT), steerable optical stylet, and an adapter configured to fit onto a standard endotracheal tube via special spring.

Referring to FIG. 13, lung isolation system 200 comprises three main components: 1) an expandable bronchial isolation tube (EBIT) 230; 2) a bifurcated adapter 260; and 3) a steerable optical stylet 20.

The EBIT 230 is an elongate (e.g. 30 cm long) endotracheal tube (having approximately a 5 mm internal diameter) that is primarily composed of nitinol wire frame tube 232 terminating proximally at a universal (e.g. 15 mm) connector 246.

Nitinol wire frame tube 232 nitinol frame made up from a plurality of nitinol segments 234 that is embedded a silicone or other membranous material 236 such that the tube 232 is both gas and liquid impermeable. The nitinol wire frame 232 has a memory such that it springs to an expanded, tubular configuration in the resting state. However, when axially loaded (as shown in FIG. 2A and 2B for EBIT 30), the frame 232 collapses and lengthens, such that it forms a catheter with an obliterated lumen and a much-reduced external diameter for easy insertion and positioning. Continuous input of force is required to keep the EBIT in the closed configuration (offsetting the natural tendency of the frame to spring into the expanded tubular shape).

The distal end 240 flares out in a shape resembling a bell, such that when expanded, the nitinol frame approximates the internal dimensions of the mainstem bronchus, minimizing gaps to improve the seal.

Referring now to FIG. 14A and FIG. 14B, radially surrounding the EBIT distal tip 240 and aperture 242 is an inflatable balloon 238 cuff configured to create a seal with the mainstem bronchus. The balloon 238 is mated to the outside diameter of the nitinol distal tip 240, such that it takes a shape similar to the bell tipped wire frame 240. Using the balloon cuff valve 248, air may be delivered to balloon 238 once the distal 240 end of the EBIT 230 is delivered to the target location within the body. The balloon cuff 238 then expands from the collapsed configuration shown in FIG. 14A, to the expanded configuration shown in FIG. 14B.

The nitinol frame 234, given its springy characteristics, takes the internal shape of the mainstem bronchus, such that the balloon 238 only needs to seal the small gaps left at the tube/bronchus interface. Furthermore, the balloon 238 surface has a roughened texture and is further adorned with fine ridges 244 to increase the friction between the balloon and airway mucosa. The combination of closer mechanical fit and high friction materials creates an ideal balloon cuff that effectively seals any gaps. Since static friction is a multiple of a) the static coefficient of friction and b) the perpendicular force between the two surfaces, the EBIT cuff's 238 enhanced friction coefficient ensures a stable fit. This design reduces possible airway injury from cuff over-inflation by requiring a lower perpendicular force (and thus cuff inflation pressure) to seal gaps and resist dislodgement and migration. The EBIT 230 is preferably a single use component that is to be discarded at the end of a case.

Figure 15:
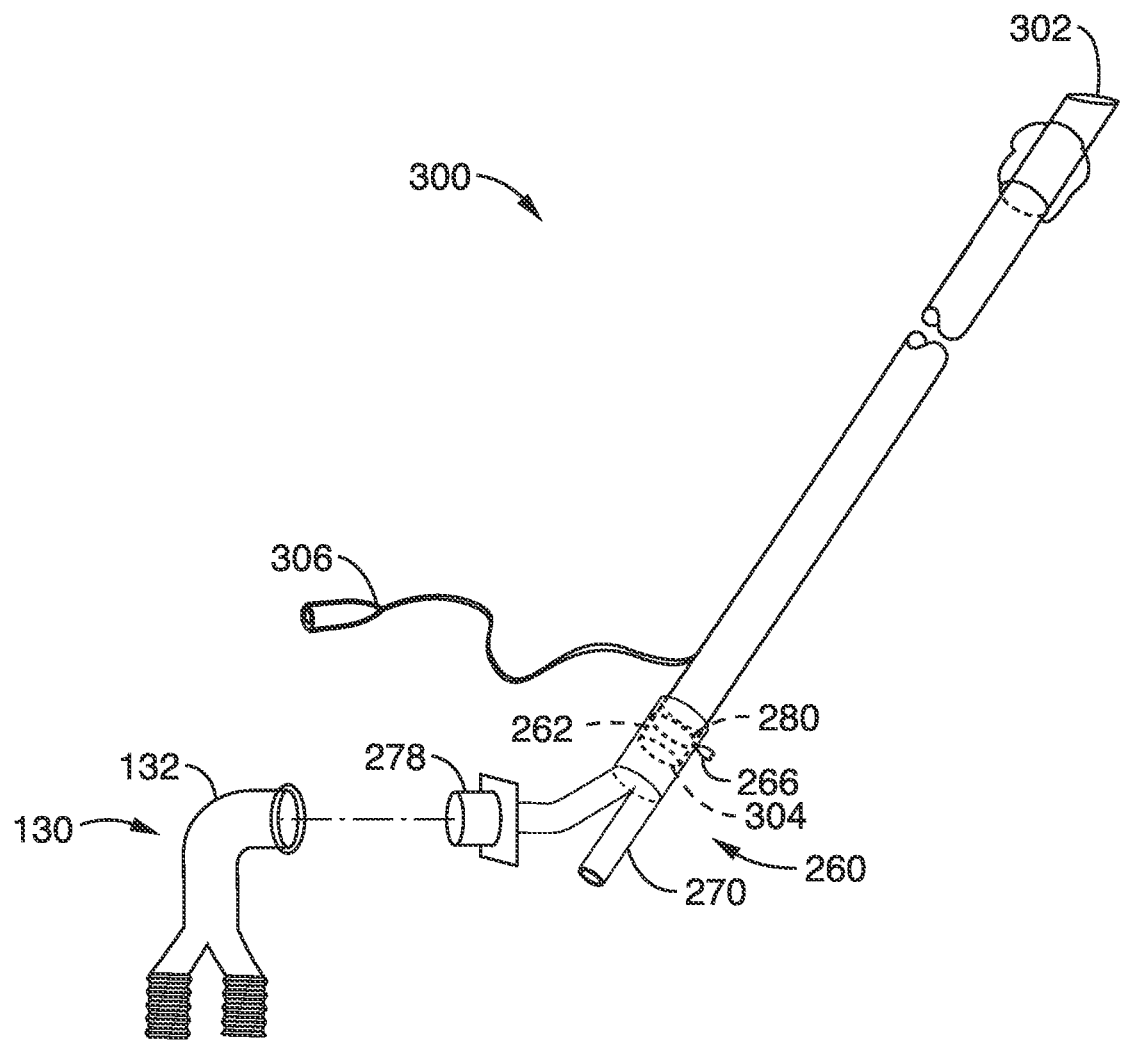
FIG. 15 shows the adapter of FIG. 13 attached over the outside diameter of endotracheal tube having the universal 15 mm connector removed.

Referring back to FIG. 13, the adapter 260 allows for the integration of the system 200 with a standard large bore single lumen endotracheal tube 300 and mechanical ventilator 130 (see also FIG. 15). In a preferred embodiment, the adapter 260 comprises a distal tube 262 that bifurcates at junction 268, to a modified "Y" configuration. The left hand lumen 276 contains a universal endotracheal tube connector (e.g. 15 mm) that is configured to attach to the mechanical ventilator 130 during use.

The right hand lumen 270 comprises the conduit aperture 274 through which the EBIT 230 is inserted and deployed. Within this lumen 274 is contained a circumferential diaphragm 272 that surrounds the inserted EBIT 230, sealing any gaps and thus preventing gas leakage during positive pressure ventilation. When the EBIT is removed, the diaphragm 272 seals the hole 274 without the need for a cap.

Referring to FIG. 15, the distal opening 264 and section 262 of adapter 260 is configured to fit over the outside diameter of the proximal end 304 of a standard plastic endotracheal tube 300 after the universal 15 mm connector has been removed (FIG. 15 and connector 42 of FIG. 8 for reference). Inside the distal end 262 of the adapter 260 lies an internal diameter spring 280 that expands to fit onto endotracheal tubes 300 of varying diameter. The spring is first depressed (stretched and opened) by engaging prongs 266 extending from slot 280 to allow insertion of the endotracheal tube 300 into the distal adapter 260. Once the spring 266 is released, internal portion 262 grips the tube 300 circumferentially and tightly, preventing disconnection and gas leak. Fitting the adapter 260 over the endotracheal tube outside diameter allows complete utilization of the endotracheal tube lumen by eliminating the 15 mm universal connector and its associated narrowing of the lumen.

The left-side bifurcation 276 of the adapter 260 comprises a standard connector 278 fitting end 132 of the ventilator 130. The adapter 260 is preferably a single use component that is to be discarded at the end of a case.

The steerable optical stylet 20 is configured to steer and position the EBIT 230 into the proper location in the tracheobronchial tree and monitor the position of the EBIT throughout the procedure. The steerable optical stylet 20 is configured to operate with EBIT 230 in a similar fashion as shown in FIG. 5 with respect to EBIT 30, and steers the EBIT 230 as detailed in FIG. 6A and FIG. 6B. As detailed in FIG. 4, the steerable distal tip 24 of stylet 20 preferably houses a video chip camera 82 as well as an LED based battery powered light source 80 for illuminating and imaging the target anatomy. The SOS 20 interfaces either via wired (e.g. USB port 96) or wireless (not shown) connection with a video system 90 comprising a display 90 and recorder/memory 94 for viewing and storing video images of the target anatomy. The disposable plastic sheath 100 shown in FIG. 7 may also be used.

Figure 16:
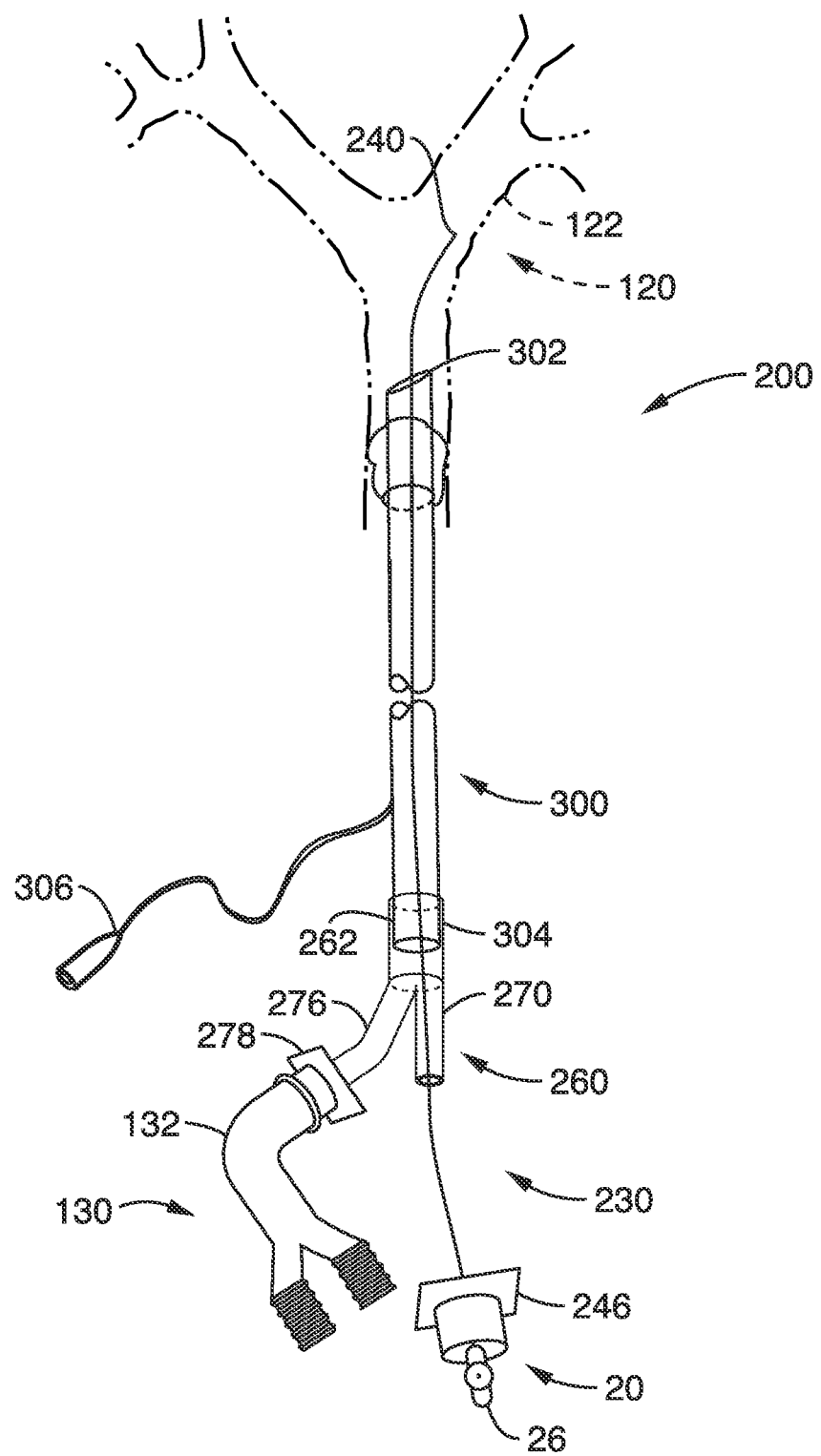
FIG. 16 shows the EBIT and steerable optical stylet assembly of FIG. 13 being steered into the right mainstem bronchus for positioning.
Figure 17:
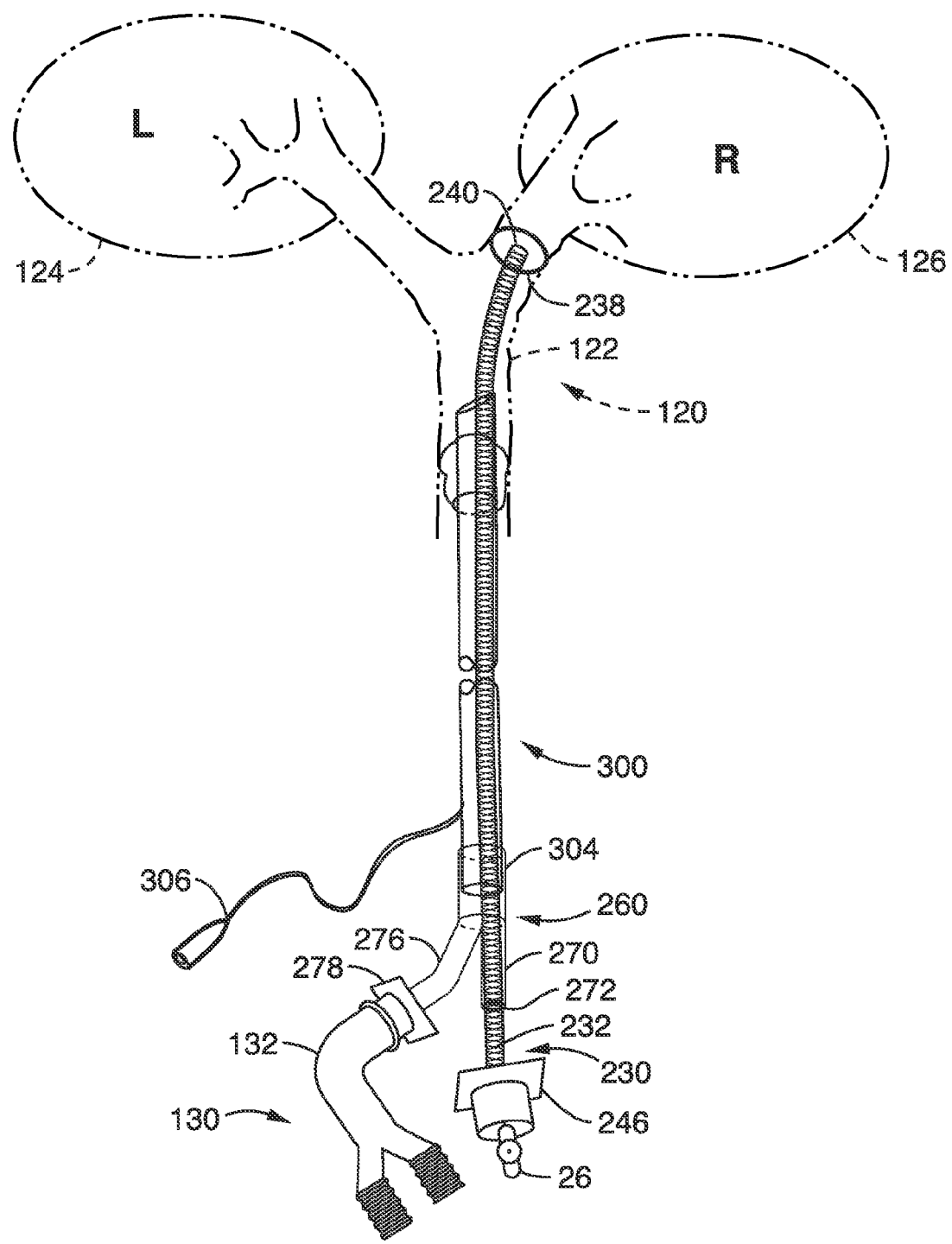
FIG. 17 shows the EBIT of FIG. 13 expanded in right mainstem in a right sided DLT configuration.

Referring to FIG. 15 through FIG. 17, the lung isolation system 200 enables lung isolation and one-lung ventilation when used in conjunction with a standard large bore single lumen endotracheal tube. When the lung isolation system 200 is deployed through a standard endotracheal tube 300, two effective lumens are created. The assembled device functions as a tube with two lumens, but instead of being parallel, the lumens are arranged in coaxial configuration (i.e. tube within a tube). The internal lumen is comprised of the EBIT 230 central lumen 242, which generally assumes the endobronchial position. The second lumen is comprised of the space created outside of and surrounding the EBIT 230, but within the central lumen of the large bore endotracheal tube 300. As shown in FIG. 16, this circumferential lumen is accessed through the left bifurcation 276 of the adapter 260, and serves as the tracheal lumen.

According to a preferred method of the technology of the present disclosure, patients set to undergo this will first undergo general endotracheal anesthesia, preferably with an 8.0 mm (or larger) endotracheal tube 140. Once the patient is anesthetized and intubated, for the present embodiment the following steps are then taken in sequence:

1) The universal 15 mm connector is removed from the standard single lumen endotracheal tube 300.

2) The adapter 260 is then attached to the endotracheal tube 300 by depressing spring 266 (FIG. 15) on the adapter 260, sliding the adapter over the outside diameter of the endotracheal tube 300, and releasing the spring 266.

3) Once the adapter 260 is securely attached to the endotracheal tube 300, the ventilator 300 is connected to the universal 15 mm connector 278 located on the left bifurcation 276 of the adapter 260, and the patient is then ventilated in a standard fashion (FIG. 16).

4) The EBIT 230 and adapter 260 are then configured (e.g. as shown in FIG. 5) for positioning into the airway 120 tracheobronchial tree 122. It can either be positioned into the right mainstem bronchus 126 or left mainstem bronchus 124, as either configuration will allow for one lung ventilation. The clinical decision on which side to place the EBIT 230 is similar to the decision of whether to use a left or right sided double lumen endotracheal tube (DLT).

5) The EBIT 230/optical stylet 20 combination is then inserted into the right-sided bifurcation 270 of the A/C 230. This orifice serves as the introducer, allowing for seamless insertion of the EBIT 230 into the airway 120 without interruption of ventilation. A rubberized o-ring or diaphragm 272 forms a seal between the EBIT's tube 232 and the A/C bifurcation aperture 274 to prevent gas leak. The EBIT 230/optical stylet 20 combination is then inserted under direct video visualization beyond distal end 302 of tube 300 and into the airway 120, where it is steered into the desired bronchus; e.g. left for "left sided DLT configuration" or right for "right sided DLT configuration" (as shown in FIG. 16 and FIG. 17).

6) Once in position, the EBIT 230 is expanded into the tubular configuration (see FIG. 14B, FIG. 17). This may be achieved via a number of means. For example, a circumferential sheath (not shown) may be used to hold the nitinol frame 232 in a compressed state, and removed to allow it to open to the tubular configurations. Alternatively, wired stylet (similar to stylet 20) may be used to close (lengthen) the frame 232, and then be removed to open it. The balloon cuff 238 is then inflated (e.g. via cuff valve 306) to engage the bronchus wall 122; FIG. 17 demonstrates the "right sided DLT configuration." Lung isolation has now been achieved. The optical stylet 20 is then withdrawn from the expanded EBIT 230.

7) Finally, one-lung ventilation is ready to be initiated. The practitioner decides which lung is to be ventilated. It will either be the lung intubated by the EBIT 230, or the other lung (not intubated by the EBIT 230). If the 15 mm universal connector 246 at the proximal end of EBIT 230 is connected to the ventilator 130, only the lung intubated by the EBIT 230 will be ventilated. If the universal 15 mm connector 278 on the left bifurcation 276 of the adapter 260 is connected to the ventilator 130 instead, only the opposite lung (not intubated by the EBIT) is ventilated. For example, let's assume the EBIT 230 is positioned in the left mainstem bronchus 124 ("left sided DLT configuration"). Attaching the ventilator 130 to the EBIT 230 would ventilate only the left lung, whereas attaching the ventilator to the adapter 260 would ventilate only the right lung.

8) To monitor EBIT 230 position throughout the case to ensure proper lung isolation, one can utilize the steerable optical stylet 20 intraoperatively, similar to the method detailed in FIG. 10.

9) An airway suction catheter 150 may also be inserted into either the EBIT 230 or the adapter left sided bifurcation 276 during one lung ventilation, depending on which lung requires suctioning (similar to FIG. 11).

To terminate one-lung ventilation and resume two lung ventilation, the EBIT balloon 238 is deflated, the EBIT tube 230 is retracted into its closed catheter-like configuration, and the ventilator 130 to the left sided adapter 278. If one-lung ventilation is not to be resumed again, the entire EBIT 230 and adapter assembly 260 may be removed, the standard universal 15 mm connector replaced back into the endotracheal tube 300, and the endotracheal tube 300 connected to the ventilator 130.

From the discussion above it will be appreciated that the technology of the present disclosure can be embodied in various ways, including the following:

1. An apparatus for lung isolation and selective lung ventilation, comprising: an expandable bronchial isolation tube (EBIT) having a central channel spanning from a proximal end and a distal end of the tube; wherein the EBIT comprises a collapsible tubular member terminating at said distal end; the collapsible tubular member having a collapsed configuration and an open tubular configuration; wherein the distal end of the EBIT comprises an expandable member having a compressed configuration and an expanded configuration; wherein the expandable member is configured to engage an internal surface at a location within a patient's airway when in the expanded configuration; and a bifurcated connector having a distal section configured for attachment to an endotracheal tube; said distal section bifurcating into two proximal lumens; wherein a first lumen of the two proximal lumens is configured to receive the EBIT in the collapsed configuration for to advancement past the endotracheal tube to the location; and wherein, upon opening of the collapsible tubular member and engagement of the expandable member at the location, ventilation may be applied to either of the two proximal lumens to selectively ventilate the patient's left and right lungs.

2. The apparatus of any previous embodiment, further comprising: a steerable stylet; wherein the steerable stylet is configured to be received within the central channel of the EBIT such that the EBIT can be collapsed around the stylet for delivery to the location; and wherein the steerable stylet is configured to steer the EBIT to the location within patient's airway.

3. The apparatus of any previous embodiment, wherein the steerable stylet comprises an optical steerable stylet having a camera disposed on the distal end of the stylet.

4. The apparatus of any previous embodiment, wherein the collapsible tubular member comprises a collapsible nitinol frame configured to spring to the open tubular configuration when in a resting state, and a membrane configured to conduct gas through the central channel.

5. The apparatus of any previous embodiment, wherein the expandable member comprises a cylindrical balloon having an outer surface configured to engage the internal surface of the airway to affect a seal with the internal surface.

6. The apparatus of any previous embodiment, wherein the outer surface of the cylindrical balloon is course to promote contact with the internal surface of the airway.

7. The apparatus of any previous embodiment, wherein the first lumen comprises an internal seal configured to mate with the EBIT when in the open tubular configuration.

8. The apparatus of any previous embodiment, wherein the proximal end of the EBIT comprises a connector configured to allow attachment of a ventilator.

9. The apparatus of any previous embodiment, wherein a second lumen of the two proximal lumens comprises a connector configured to allow attachment of a ventilator.

10. The apparatus of any previous embodiment: wherein the expandable member is configured to engage a bronchus wall of the airway; wherein attachment of a ventilator to the proximal end of the EBIT ventilates a lung in communication with the engaged bronchus; and wherein attachment of a ventilator to the second lumen ventilates a lung in communication with a bronchus not engaged by the expandable member.

11. A system for lung isolation and selective lung ventilation, comprising: an expandable bronchial isolation tube (EBIT) having a central channel spanning from a proximal end and a distal end of the tube; wherein the EBIT comprises a collapsible tubular member terminating at said distal end; the collapsible tubular member having a collapsed configuration and an open tubular configuration; wherein the distal end of the EBIT comprises an expandable member having a compressed configuration and an expanded configuration; wherein the expandable member is configured to engage an internal surface at a location within a patient's airway when in the expanded configuration; a bifurcated connector having a distal section configured for attachment to an endotracheal tube; said distal section bifurcating into two proximal lumens; wherein a first lumen of the two proximal lumens is configured to receive the EBIT in the collapsed configuration for advancement past the endotracheal tube to the location; wherein, upon opening of the collapsible tubular member and engagement of the expandable member at the location, ventilation may be applied to either of the two proximal lumens to selectively ventilate the patient's left and right lungs; and a steerable stylet; wherein the steerable stylet is configured to be received within the central channel of the EBIT such that the EBIT can be collapsed around the stylet for delivery to the location; and wherein the steerable stylet is configured to steer the EBIT to the location within patient's airway.

12. The system of any previous embodiment, wherein the steerable stylet comprises an optical steerable stylet having a camera disposed on the distal end of the stylet.

13. The system of any previous embodiment, wherein the collapsible tubular member comprises a collapsible nitinol frame configured to spring to the open tubular configuration when in a resting state, and a membrane configured to conduct gas through the central channel.

14. The system of any previous embodiment, wherein the expandable member comprises a cylindrical balloon having an outer surface configured to engage the internal surface of the airway to affect a seal with the internal surface.

15. The system of any previous embodiment, wherein the outer surface of the cylindrical balloon is course to promote contact with the internal surface of the airway.

16. The system of any previous embodiment, wherein the first lumen comprises an internal seal configured to mate with the EBIT when in the open tubular configuration.

17. The system of any previous embodiment, wherein the proximal end of the EBIT comprises a connector configured to allow attachment of a ventilator.

18. The system of any previous embodiment, wherein a second lumen of the two proximal lumens comprises a connector configured to allow attachment of a ventilator.

19. The system of any previous embodiment: wherein the expandable member is configured to engage a bronchus wall of the airway; wherein attachment of a ventilator to the proximal end of the EBIT ventilates a lung in communication with the engaged bronchus; and wherein attachment of a ventilator to the second lumen ventilates a lung in communication with a bronchus not engaged by the expandable member.

20. A method for lung isolation and selective lung ventilation; comprising: inserting a distal end of an endotracheal tube into an airway of the patient; coupling a distal section of a bifurcated connector to a proximal end of the endotracheal tube, the distal section bifurcating into two proximal lumens; receiving an expandable bronchial isolation tube (EBIT) in a collapsed configuration through a first lumen of the two proximal lumens and advancing the EBIT past the distal end endotracheal tube to a location within the airway; opening the EBIT to an open tubular configuration; expanding an expandable member on the distal end of the EBIT to engage an internal surface at the location within a patient's airway; and applying ventilation to either of the two proximal lumens to selectively ventilate the patient's left and right lungs.

21. The method of any previous embodiment, wherein receiving an expandable bronchial isolation tube (EBIT) comprises: positioning a steerable stylet within a central channel of the EBIT; collapsing a tubular section of the EBIT around the stylet for delivery to the location; inserting the collapsed EBIT and steerable stylet into the first lumen;

and steering the collapsed EBIT with the steerable stylet to the location within patient's airway.

22. The method of any previous embodiment, wherein the steerable stylet comprises an optical steerable stylet having a camera disposed on the distal end of the stylet, the method further comprising: optically guiding the collapsed EBIT to the location.

23. The method of any previous embodiment, wherein the first lumen comprises an internal seal configured to mate with the EBIT when in the open tubular configuration.

24. The method of any previous embodiment, wherein engaging an internal surface at the location comprises engaging a bronchus wall of the airway.

25. The method of any previous embodiment, wherein applying ventilation to either of the two proximal lumens comprises: coupling a proximal end of the EBIT to a ventilator; and ventilating the proximal end of the EBIT to ventilate a lung in communication with the engaged bronchus.

26. The method of any previous embodiment, wherein applying ventilation to either of the two proximal lumens comprises: coupling a second lumen of the two proximal lumens a ventilator; and ventilating the second lumen to ventilate a lung in communication with a bronchus not engaged by the expandable member.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. An apparatus for lung isolation and selective lung ventilation, comprising:
   an expandable bronchial isolation tube (EBIT) having a central channel spanning from a proximal end and a distal end of the tube;
   wherein the EBIT comprises a collapsible tubular member terminating at said distal end;
   the collapsible tubular member having a collapsed configuration and an open tubular configuration, wherein the tubular member collapses in response to applying an axial load and opens in response to removing the axial load;
   wherein the distal end of the EBIT comprises an expandable member having a compressed configuration and an expanded configuration;
   wherein the expandable member is configured to engage an internal surface at a location within a patient's airway when in the expanded configuration; and
   a bifurcated connector having a distal section configured for attachment to an endotracheal tube;
   said distal section bifurcating into two proximal lumens;
   wherein a first lumen of the two proximal lumens is configured to receive the EBIT in the collapsed configuration for to advancement past the endotracheal tube to the location; and
   wherein, upon opening of the collapsible tubular member and engagement of the expandable member at the location, ventilation is applied to either of the two proximal lumens to selectively ventilate the patient's left and right lungs.

2. An apparatus as recited in claim 1, further comprising:
   a steerable stylet;
   wherein the steerable stylet is configured to be received within the central channel of the EBIT such that the EBIT can be collapsed around the stylet for delivery to the location; and
   wherein the steerable stylet is configured to steer the EBIT to the location within patient's airway.

3. An apparatus as recited in claim 2, wherein the steerable stylet comprises an optical steerable stylet having a distal end with a camera disposed on the distal end of the stylet.

4. An apparatus as recited in claim 1, wherein the collapsible tubular member comprises a collapsible nitinol frame configured to spring to the open tubular configuration when in a resting state, and a membrane configured to conduct gas through the central channel.

5. An apparatus as recited in claim 1, wherein the expandable member comprises a cylindrical balloon having an outer surface configured to engage the internal surface of the airway to affect a seal with the internal surface.

6. An apparatus as recited in claim 5, wherein the outer surface of the cylindrical balloon is course to promote contact with the internal surface of the airway.

7. An apparatus as recited in claim 1, wherein the first lumen comprises an internal seal configured to mate with the EBIT when in the open tubular configuration.

8. An apparatus as recited in claim 7, wherein the proximal end of the EBIT comprises a connector configured to allow attachment of a ventilator.

9. An apparatus as recited in claim 8, wherein a second lumen of the two proximal lumens comprises a connector configured to allow attachment of a ventilator.

10. An apparatus as recited in claim 9:
    wherein the expandable member is configured to engage a bronchus wall of the airway;
    wherein attachment of a ventilator to the proximal end of the EBIT ventilates a lung in communication with the engaged bronchus; and
    wherein attachment of a ventilator to the second lumen ventilates a lung in communication with a bronchus not engaged by the expandable member.

11. A system for lung isolation and selective lung ventilation, comprising:
    an expandable bronchial isolation tube (EBIT) having a central channel spanning from a proximal end and a distal end of the tube;
    wherein the EBIT comprises a collapsible tubular member terminating at said distal end;
    the collapsible tubular member having a collapsed configuration and an open tubular configuration, wherein the tubular member collapses in response to applying an axial load and opens in response to removing the axial load;

wherein the distal end of the EBIT comprises an expandable member having a compressed configuration and an expanded configuration;
wherein the expandable member is configured to engage an internal surface at a location within a patient's airway when in the expanded configuration;
a bifurcated connector having a distal section configured for attachment to an endotracheal tube;
said distal section bifurcating into two proximal lumens;
wherein a first lumen of the two proximal lumens is configured to receive the EBIT in the collapsed configuration for advancement past the endotracheal tube to the location;
wherein, upon opening of the collapsible tubular member and engagement of the expandable member at the location, ventilation is applied to either of the two proximal lumens to selectively ventilate the patient's left and right lungs; and
a steerable stylet;
wherein the steerable stylet is configured to be received within the central channel of the EBIT such that the EBIT can be collapsed around the stylet for delivery to the location; and
wherein the steerable stylet is configured to steer the EBIT to the location within patient's airway.

12. A system as recited in claim 11, wherein the steerable stylet comprises an optical steerable stylet having a distal end with a camera disposed on the distal end of the stylet.

13. A system as recited in claim 11, wherein the collapsible tubular member comprises a collapsible nitinol frame configured to spring to the open tubular configuration when in a resting state, and a membrane configured to conduct gas through the central channel.

14. A system as recited in claim 11, wherein the expandable member comprises a cylindrical balloon having an outer surface configured to engage the internal surface of the airway to affect a seal with the internal surface.

15. A system as recited in claim 14, wherein the outer surface of the cylindrical balloon is course to promote contact with the internal surface of the airway.

16. A system as recited in claim 11, wherein the first lumen comprises an internal seal configured to mate with the EBIT when in the open tubular configuration.

17. A system as recited in claim 16, wherein the proximal end of the EBIT comprises a connector configured to allow attachment of a ventilator.

18. A system as recited in claim 17, wherein a second lumen of the two proximal lumens comprises a connector configured to allow attachment of a ventilator.

19. A system as recited in claim 18:
wherein the expandable member is configured to engage a bronchus wall of the airway;
wherein attachment of a ventilator to the proximal end of the EBIT ventilates a lung in communication with the engaged bronchus; and
wherein attachment of a ventilator to the second lumen ventilates a lung in communication with a bronchus not engaged by the expandable member.

20. A method for lung isolation and selective lung ventilation; comprising:
inserting a distal end of an endotracheal tube into an airway of the patient;
coupling a distal section of a bifurcated connector to a proximal end of the endotracheal tube, the distal section bifurcating into two proximal lumens;
receiving an expandable bronchial isolation tube (EBIT) in a collapsed configuration through a first lumen of the two proximal lumens and advancing the EBIT past the distal end endotracheal tube to a location within the airway;
opening the EBIT to an open tubular configuration;
wherein the EBIT collapses in response to applying an axial load and opens in response to removing the axial load;
expanding an expandable member on the distal end of the EBIT to engage an internal surface at the location within a patient's airway; and
applying ventilation to either of the two proximal lumens to selectively ventilate the patient's left and right lungs.

21. A method as recited in claim 20, wherein receiving an expandable bronchial isolation tube (EBIT) comprises:
positioning a steerable stylet within a central channel of the EBIT;
collapsing a tubular section of the EBIT around the stylet for delivery to the location;
inserting the collapsed EBIT and steerable stylet into the first lumen; and
steering the collapsed EBIT with the steerable stylet to the location within patient's airway.

22. A method as recited in claim 21, wherein the steerable stylet comprises an optical steerable stylet having a distal end with a camera disposed on the distal end of the stylet, the method further comprising:
optically guiding the collapsed EBIT to the location.

23. A method as recited in claim 20, wherein the first lumen comprises an internal seal configured to mate with the EBIT when in the open tubular configuration.

24. A method as recited in claim 23, wherein engaging an internal surface at the location comprises engaging a bronchus wall of the airway.

25. A method as recited in claim 24, wherein applying ventilation to either of the two proximal lumens comprises:
coupling a proximal end of the EBIT to a ventilator; and
ventilating the proximal end of the EBIT to ventilate a lung in communication with the engaged bronchus.

26. A method as recited in claim 24, wherein applying ventilation to either of the two proximal lumens comprises:
coupling a second lumen of the two proximal lumens a ventilator; and ventilating the second lumen to ventilate a lung in communication with a bronchus not engaged by the expandable member.

* * * * *